United States Patent
Zhao et al.

(10) Patent No.: US 10,947,171 B2
(45) Date of Patent: *Mar. 16, 2021

(54) PROCESS FOR SEPARATING HYDROGEN FROM AN OLEFIN HYDROCARBON EFFLUENT VAPOR STREAM

(71) Applicant: EnFlex, Inc., Houston, TX (US)

(72) Inventors: James Zhao, Houston, TX (US); Shukui Zhao, Katy, TX (US)

(73) Assignee: Enflex, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,118

(22) Filed: Apr. 27, 2020

(65) Prior Publication Data
US 2020/0275630 A1    Sep. 3, 2020

Related U.S. Application Data

(63) Continuation of application No. 15/600,758, filed on May 21, 2017, now Pat. No. 10,633,305.

(51) Int. Cl.
| | | |
|---|---|---|
| *F25J 1/02* | (2006.01) | |
| *C07C 5/327* | (2006.01) | |
| *C07C 7/00* | (2006.01) | |
| *C07C 7/04* | (2006.01) | |
| *F25J 3/06* | (2006.01) | |

(Continued)

(52) U.S. Cl.
CPC ............... *C07C 5/327* (2013.01); *A01H 5/10* (2013.01); *A01H 6/4684* (2018.05); *C07C 7/005* (2013.01); *C07C 7/04* (2013.01); *F25J 3/062* (2013.01); *F25J 3/0645* (2013.01); *F25J 3/0655* (2013.01); *F25J 2210/04* (2013.01); *F25J 2210/12* (2013.01); *F25J 2210/62* (2013.01); *F25J 2215/02* (2013.01); *F25J 2215/04* (2013.01); *F25J 2215/64* (2013.01); *F25J 2230/20* (2013.01); *F25J 2230/30* (2013.01); *F25J 2230/32* (2013.01); *F25J 2235/60* (2013.01); *F25J 2245/02* (2013.01); *F25J 2270/06* (2013.01); *F25J 2270/904* (2013.01)

(58) Field of Classification Search
CPC ..... C07C 11/02–10; C07C 7/005; C07C 7/04; F25J 3/0655; F25J 1/0037; F25J 1/0288; F25J 2230/20; F25J 1/0202; F25J 1/04; F25J 2210/12; F25J 3/062; F25J 3/0645; F25J 2270/06
See application file for complete search history.

(56) References Cited

U.S. PATENT DOCUMENTS

| | | | | |
|---|---|---|---|---|
| 5,592,831 A | * | 1/1997 | Bauer | F25J 3/0223 62/625 |
| 6,333,445 B1 | * | 12/2001 | O'Brien | F25J 3/065 585/809 |
| 7,219,513 B1 | | 5/2007 | Mostafa | |

OTHER PUBLICATIONS

USPTO Non-Final Office Action for U.S. Appl. No. 15/600,758 dated Apr. 15, 2019.

(Continued)

*Primary Examiner* — Brian M King
(74) *Attorney, Agent, or Firm* — Tumey, L.L.P.; Eric M. Adams

(57) ABSTRACT

One or more specific embodiments disclosed herein includes a method for separating hydrogen from an olefin hydrocarbon rich compressed effluent vapor stream, employing a single heat exchanger, multiple gas-liquid separators, multiple expander/compressor sets, and a rectifier attached to a liquid product drum.

8 Claims, 6 Drawing Sheets

(51) Int. Cl.
*A01H 6/46* (2018.01)
*A01H 5/10* (2018.01)

(56) References Cited

OTHER PUBLICATIONS

USPTO Final Office Action for U.S. Appl. No. 15/600,758 dated Sep. 25, 2019.
USPTO Notice of Allowance for U.S. Appl. No. 15/600,758 dated Dec. 26, 2019.
USPTO Corrected Notice of Allowance for U.S. Appl. No. 15/600,758 dated Feb. 19, 2020.
USPTO Issue Notification for U.S. Appl. No. 15/600,758 dated Apr. 8, 2020.

* cited by examiner

PROCESS FOR SEPARATING HYDROGEN FROM AN OLEFIN HYDROCARBON EFFLUENT VAPOR STREAM

CROSS-REFERENCE TO RELATED APPLICATIONS

This application is a continuation of U.S. application Ser. No. 15/600,758 filed on May 21, 2017, which is herein incorporated by reference in its entirety.

STATEMENT REGARDING FEDERALLY SPONSORED RESEARCH OR DEVELOPMENT

Not applicable.

BACKGROUND

1. Field of Inventions

The field of this application and any resulting patent is processes and systems for separating hydrogen from an olefin hydrocarbon vapor stream.

2. Description of Related Art

Various processes and systems have been proposed and utilized for separating hydrogen from an olefin hydrogen rich compressed effluent vapor stream, including some of the processes and systems disclosed in the references appearing on the face of this patent. However, those processes and systems lack all the steps or features of the processes and systems covered by any patent claims below. As will be apparent to a person of ordinary skill in the art, any processes and systems covered by claims of the issued patent solve many of the problems that prior art processes and systems have failed to solve. Also, the processes and systems covered by at least some of the claims of this patent have benefits that could be surprising and unexpected to a person of ordinary skill in the art based on the prior art existing at the time of invention.

SUMMARY

One or more specific embodiments disclosed herein includes a process for the separation of hydrogen from an olefin hydrocarbon rich compressed effluent vapor stream from a dehydrogenation unit, comprising cooling a compressed effluent vapor stream in a heat exchanger; separating hydrogen from olefin and heavy paraffinic components in the cooled compressed effluent vapor stream in a first separator to provide a first vapor stream and a first liquid stream; cooling the first vapor stream in the heat exchanger; separating hydrogen from olefin and heavy paraffinic components in the cooled first vapor stream in a second separator to provide a second vapor stream and a second liquid stream; warming the second vapor stream in the heat exchanger; isentropically expanding, in a high-pressure expander, the second vapor stream, wherein the pressure and temperature of the second vapor stream are lowered; warming the second vapor stream in the heat exchanger; compressing, in a high-pressure compressor, the second vapor stream; cooling the second vapor stream in a first discharge cooler; dividing the second vapor stream into a gas product and a split stream; withdrawing the gas product; compressing, in a low-pressure compressor, the split stream; cooling the split stream in a second discharge cooler and further cooling the split stream in the heat exchanger; isentropically expanding, in a low-pressure expander, the split stream, wherein the pressure and temperature of the split stream are lowered; cooling a liquid paraffinic stream in the heat exchanger; combining the cooled liquid paraffinic stream with the expanded split stream to provide a combined feed; vaporizing the combined feed in the heat exchanger; withdrawing the vaporized combined feed; lowering the pressure of the first liquid stream in a control valve; partially vaporizing the first liquid stream in the heat exchanger; flashing the partially vaporized first liquid stream in a liquid product drum to provide a hydrogen-rich gas, which travels to a rectifier connected to the liquid product drum; combining the hydrogen-rich gas and the second liquid stream in the rectifier, further purifying the hydrogen-rich gas; warming the hydrogen-rich gas from the rectifier in the heat exchanger to provide a flashed vapor stream; pumping a third liquid stream from the liquid product drum to the heat exchanger, wherein it is warmed; and providing a liquid product.

One or more specific embodiments disclosed herein includes a process for the separation of hydrogen from an olefin hydrocarbon rich compressed effluent vapor stream from a dehydrogenation unit, comprising separating hydrogen from olefin and heavy paraffinic components in the compressed effluent vapor stream to provide a first vapor stream and a first liquid stream; separating hydrogen from olefin and heavy paraffinic components in the first vapor stream to provide a second vapor stream and a second liquid stream; expanding and compressing the second vapor stream; dividing the second vapor stream into a gas product and a split stream; compressing and expanding the split stream; lowering the pressure of the first liquid stream; partially vaporizing the first liquid stream; flashing the partially vaporized first liquid stream in a liquid product drum to provide a hydrogen-rich gas; and combining the hydrogen-rich gas and the second liquid stream in a rectifier.

One or more specific embodiments disclosed herein includes a process for the separation of hydrogen from an olefin hydrocarbon rich compressed effluent vapor stream from a dehydrogenation unit, comprising separating hydrogen from olefin and heavy paraffinic components in the compressed effluent vapor stream to provide a first vapor stream and a first liquid stream; separating hydrogen from olefin and heavy paraffinic components in the first vapor stream to provide a second vapor stream and a second liquid stream; isentropically expanding, in a high-pressure expander, the second vapor stream; compressing, in a high-pressure compressor, the second vapor stream; dividing the second vapor stream into a gas product and a split stream; compressing, in a low-pressure compressor, the split stream; and isentropically expanding, in a low-pressure expander, the split stream.

DETAILED DESCRIPTION

1. Introduction

Figure 1:
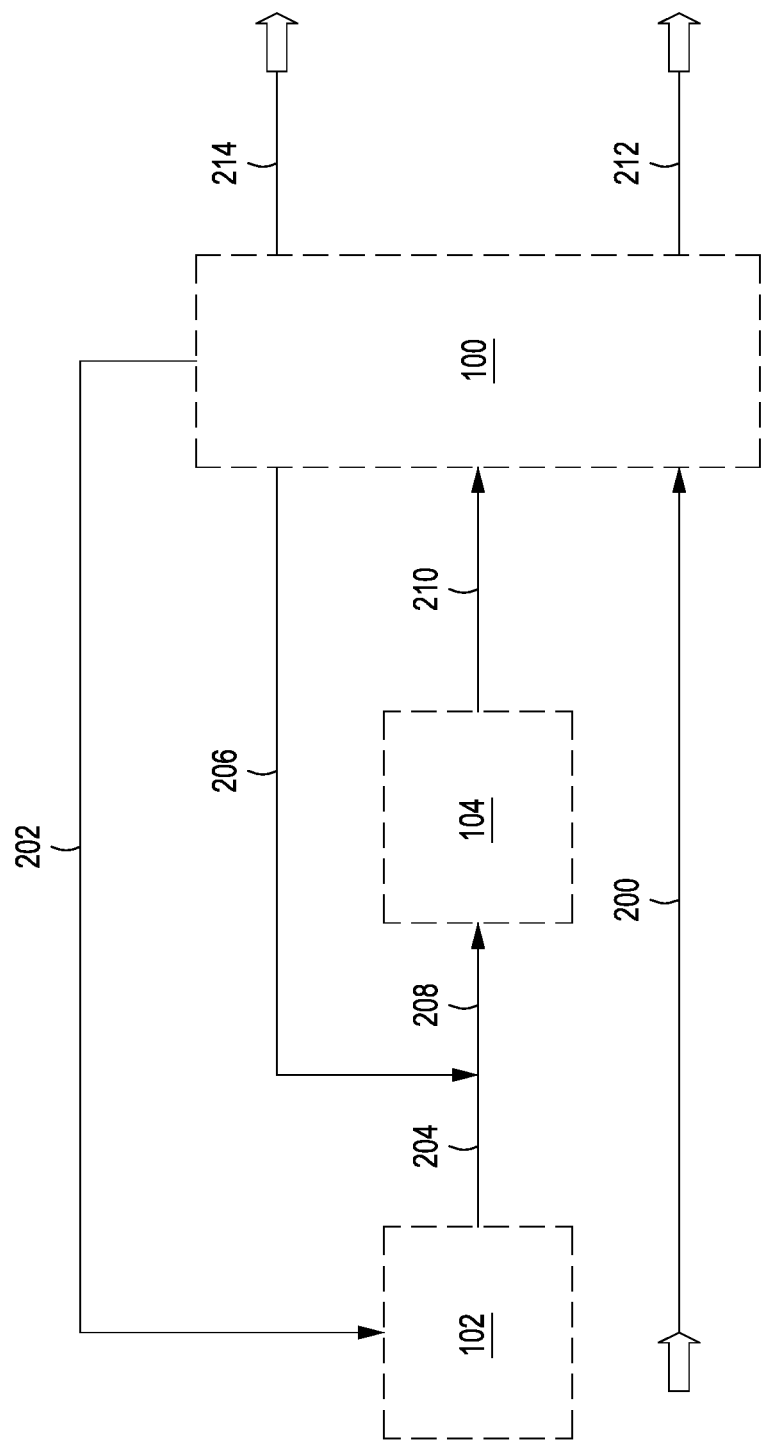
FIG. 1 is a schematic illustration, block flow diagram of a system for hydrogen separation shown as a part on and in an overall dehydrogenation system.

A detailed description will now be provided. The purpose of this detailed description, which includes the drawings, is to satisfy the statutory requirements of 35 U.S.C. § 112. For example, the detailed description includes a description of the inventions defined by the claims and sufficient information that would enable a person having ordinary skill in the art to make and use the inventions. In the figures, like elements are generally indicated by like reference numerals regardless of the view or figure in which the elements appear. The figures are intended to assist the description and to provide a visual representation of certain aspects of the subject matter described herein. The figures are not all necessarily drawn to scale, nor do they show all the structural details of the systems, nor do they limit the scope of the claims.

Each of the appended claims defines a separate invention which, for infringement purposes, is recognized as including equivalents of the various elements or limitations specified in the claims. Depending on the context, all references below to the "invention" may in some cases refer to certain specific embodiments only. In other cases, it will be recognized that references to the "invention" will refer to the subject matter recited in one or more, but not necessarily all, of the claims. Each of the inventions will now be described in greater detail below, including specific embodiments, versions, and examples, but the inventions are not limited to these specific embodiments, versions, or examples, which are included to enable a person having ordinary skill in the art to make and use the inventions when the information in this patent is combined with available information and technology. Various terms as used herein are defined below, and the definitions should be adopted when construing the claims that include those terms, except to the extent a different meaning is given within the specification or in express representations to the Patent and Trademark Office. (PTO). To the extent a term used in a claim is not defined below or in representations to the PTO, it should be given the broadest definition persons having skill in the art have given that term as reflected in any printed publication, dictionary, or issued patent.

2. Selected Definitions

Certain claims include one or more of the following terms which, as used herein, are expressly defined below.

The term "olefin hydrocarbon" as used herein is defined as an unsaturated hydrocarbon that contains at least one carbon-carbon double bond. The term "compressed effluent vapor stream" as used herein is defined as an olefin-hydrogen effluent gas stream from a feed compressor. In certain embodiments disclosed herein, a combined feed enters a dehydrogenation unit to create an effluent gas stream that contains hydrogen, olefins, and heavy hydrocarbon components. The effluent gas stream in these embodiments is a low-pressure effluent stream. An example of a dehydrogenation unit is OLEFLEX™, which is a brand name for a dehydrogenation unit (OLEFLEX™ is a trademark of UOP Inc. of Des Plaines, Ill.).

In certain embodiments disclosed herein, the compressed effluent vapor stream is referred to as a reactor effluent. Further, in certain embodiments, the reactor effluent enters a process for hydrogen separation at 35° C.-52° C. and 0.5-1.2 MPa(g).

The term "compressor" as used herein is defined as a mechanical device that increases the pressure of a gas by reducing its volume. In certain embodiments disclosed herein, the feed compressor is also referred to as the reactor effluent compressor unit.

The term "heat exchanger" as used herein is defined as a device that transfers or "exchanges" heat from one matter to another. In certain embodiments disclosed herein, the heat exchanger is referred to as the integrated main heat exchanger. Further, in certain embodiments disclosed herein, there may be more than one heat exchanger or only one heat exchanger. Also, in certain embodiments, the heat exchanger may be composed of brazed aluminum heat exchanger cores. In at least one specific embodiment disclosed herein, the integrated main heat exchanger has warm stream passes, and it has cold stream passes. Additionally, in certain embodiments with more than one heat exchanger, the heat exchangers may be configured in series or parallel.

The term "separator" as used herein is defined as a device used to separate hydrogen from olefin and heavy paraffinic components. In certain embodiments disclosed herein, gravity is used in a vertical vessel to cause liquid to settle to the bottom of the vessel, where the liquid is withdrawn. In the same embodiments, the gas part of the mixture travels through a gas outlet at the top of the vessel. Further, in certain embodiments disclosed herein, there is more than one separator employed. In certain embodiments disclosed herein, each separator results in a majority of the olefin and paraffinic components being condensed to liquid and the hydrogen remaining vapor. A "paraffin hydrocarbon" is a saturated hydrocarbon having a general formula $C_nH_{2n+2}$. For example, in one embodiment disclosed herein, an outlet stream enters a second separator and results in 99.8% vapor and 0.2% liquid.

The term "first vapor stream" as used herein is mainly hydrogen gas. In one specific embodiment disclosed herein, the first vapor stream is vapor stream from the first stage cold gas-liquid separator.

The term "first liquid stream" as used herein is composed of condensed olefin and paraffinic components. In certain embodiments disclosed herein, the first liquid stream is an olefin-rich liquid stream. Further, in certain embodiments disclosed herein, the first liquid stream is liquid stream from the first stage cold gas-liquid separator.

The term "second vapor stream" as used herein is composed of mainly hydrogen gas. In certain embodiments disclosed herein, the second vapor stream has a temperature of −115° C. Further, in certain embodiments disclosed herein, the second vapor stream is a vapor stream from the second stage cold gas-liquid separator.

The term "second liquid stream" as used herein is composed of olefin and paraffinic components in liquid form. In one specific embodiment disclosed herein, the second liquid stream is a liquid stream from the second stage cold gas-liquid separator.

The term "expander" as used herein is defined as a centrifugal or axial flow turbine through which a gas is isentropically expanded. In one specific embodiment disclosed herein, cryogenic temperatures are achieved from refrigeration by expanding a high-pressure effluent gas stream using two-stage expanders. The term "cryogenic" as used herein is an adjective which means being or related to very low temperatures. The term "refrigeration" as used herein is defined as the process of moving heat from one location to another in controlled conditions.

An example of one type of expander configuration is an expander/compressor configuration, which can be two independent expander/compressor sets. In this example of an expander/compressor configuration, the two sets may be either two separate magnetic bearing type expander/compressor sets or oil bearing type sets that share a common lube oil system. For the expander configuration with two separate expander/compressor sets, one set may be called a high-pressure expander/compressor set that is configured as "post-compression." Another set may be called a low-pressure expander/compressor set that is configured as "pre-compression." "Post-compression" means that the compressor is set to compress the gas stream after expansion. "Pre-compression" means that the compressor is set to compress the gas stream before expansion. In certain embodiments disclosed herein, the composition and mass flow of the stream to the high-pressure expander and the high-pressure compressor remain substantially unchanged. Further, in the same embodiments, the composition and mass flow of the stream to the low-pressure expander and the low-pressure compressor remain substantially unchanged.

In other embodiments, a booster compressor may be added at the discharge of a high-pressure compressor. The term "booster compressor" as used herein refers to an additional compressor that provides additional pressure. In one specific embodiment disclosed herein, a booster compressor is added to achieve the required refrigeration for an effluent gas stream. Further, in the same embodiment, the booster compressor may be an independent compressor driven by either electrical motor or another type of driver. The term "motor" as used herein is defined as an electrical machine that converts electrical energy into mechanical energy.

In other embodiments, the high-pressure expander, the low-pressure expander, the high-pressure compressor, and the low-pressure compressor are mounted to a common bull gear to form a non-driver I-Compander. The term "bull gear" as used herein is defined as any large driving gear among smaller gears. In yet another embodiment, an electrical motor may be added to the bull gear to provide additional power for the compressor(s) to boost the pressure of a gas stream.

Another example of an expander configuration is an expander/electric generator configuration. The term "electric generator" as used herein is defined as a device that converts mechanical energy into electrical energy. In certain embodiments disclosed herein, there may be two separate expander/electric generator sets. Further, in those embodiments, the output power from the high-pressure expander drives its corresponding electric generator to produce electricity. Likewise, in those same embodiments, the output power from the low-pressure expander drives its corresponding electric generator to produce electricity.

The term "gas product" as used herein is defined as a hydrogen-rich gas product stream, which is sent to a downstream production facility. In one specific embodiment disclosed herein, the gas product is net gas product. In one example, the gas product contains primarily the hydrogen as well as the methane and ethane lighter hydrocarbons from the reactor effluent stream minus the material produced internally as recycle gas. In this example, the specifications for the gas product are as follows:

| PDH Unit | |
| --- | --- |
| Hydrogen, mole percent minimum | 92.5 |
| Total $C_{3+}$ olefins, mole % maximum | 0.055 |
| Temperature, C. | 36 |
| Pressure, MPa(g) | 0.60 |

The term "split stream" as used herein refers to a hydrogen-rich stream. In one specific embodiment disclosed herein, the split stream is a recycle gas. In one example, the recycle gas meets the following specifications:

| PDH Unit | |
| --- | --- |
| Hydrogen, mole percent minimum | 92.5 |
| Total Olefins, mole percent | 0.1 maximum |
| C3+ Olefins, mole percent | 0.05 maximum |

The term "liquid paraffinic stream" as used herein refers to a liquid hydrocarbon stream of primarily propane, isobutane, or a mixture of primarily both. Propane is a three-carbon alkane with the molecular formula $C_3H_8$. Isobutane is the simplest alkane with a tertiary carbon, and it has the molecular formula $C_4H_{10}$. In one specific embodiment disclosed herein, the liquid paraffinic stream is the fresh feed. In one example, the liquid paraffinic stream has a temperature of 52° C. and a pressure of 2.06 MPa(g).

The term "control valve" as used herein is defined as a valve used to control fluid flow by varying the size of the flow passage. In one specific embodiment disclosed herein, the control valve is used to lower the pressure of the fluid flow. The term "liquid product drum" as used herein is defined as a device used to separate a vapor-liquid mixture. In certain embodiments disclosed herein, a liquid product drum is attached to a rectifier. In these certain embodiments, the liquid product drum is used for flashing a partially vaporized liquid stream. The term "flashing" as used herein refers to "flash evaporation," which is defined as the partial vapor that occurs when a saturated liquid stream undergoes a reduction in pressure by passing through a throttling valve or other throttling device. In one example, the temperature of the liquid product drum is maintained at around 0° C. so that the liquid product drum may be composed of carbon steel.

In one specific embodiment, once in the liquid product drum, light components such as hydrogen, methane, and ethane, flash out from the liquid and travel upward through a rectifier located on top of the liquid product drum. The term "rectifier" as used herein is defined as a packed column used for "rectification." In "rectification," vapor and liquid are passed countercurrent to one another through a special apparatus, sometimes known as a rectifier, in which there are multiple points of contact between the two phases. The countercurrent movement is accompanied by heat and mass exchanges. In one example, the rectifier is a hollow vertical cylinder, within which there are irregularly shaped materials, known collectively as packing. The packing is used to enlarge the vapor-liquid interface.

The term "final liquid product" as used herein refers to an olefin-rich liquid product stream. In one specific embodiment disclosed herein, the final liquid product is liquid product stream 307. In one example, the final liquid product contains primarily the propylene and heavier hydrocarbons from a reactor effluent stream, meeting the following specifications:

| | |
|---|---|
| Propane + propylene recovery, % | 99.9 |
| Temperature, C. | 50 ± 5° C. |
| Pressure, MPa(g) | 4.0 |

The "flashed vapor stream" is the vapor from the liquid product drum. In certain embodiments disclosed herein, the flashed vapor stream may be recycled back to the reactor effluent compressor unit for recovery of any hydrocarbons in the flashed vapor stream.

The term "coldbox" as used herein is defined as a box designed to contain low-temperature and cryogenic equipment and parts. In certain embodiments disclosed herein, the coldbox is filled with insulation material and purged with nitrogen to provide cold insulation. In certain embodiments, the coldbox may contain the heat exchanger, the separators, the liquid product drum and rectifier, as well as the associated piping. In the same embodiments, control valves can either be enclosed within or installed outside of the coldbox.

3. Certain Specific Embodiments

Now, certain specific embodiments are described, which are by no means an exclusive description of the inventions. Other specific embodiments, including those referenced in the drawings, are encompassed by this application and any patent that issues therefrom.

One or more specific embodiments disclosed herein includes a process for the separation of hydrogen from an olefin hydrocarbon rich compressed effluent vapor stream from a dehydrogenation unit, comprising cooling a compressed effluent vapor stream in a heat exchanger; separating hydrogen from olefin and heavy paraffinic components in the cooled compressed effluent vapor stream in a first separator to provide a first vapor stream and a first liquid stream; cooling the first vapor stream in the heat exchanger; separating hydrogen from olefin and heavy paraffinic components in the cooled first vapor stream in a second separator to provide a second vapor stream and a second liquid stream; warming the second vapor stream in the heat exchanger; isentropically expanding, in a high-pressure expander, the second vapor stream, wherein the pressure and temperature of the second vapor stream are lowered; warming the second vapor stream in the heat exchanger; compressing, in a high-pressure compressor, the second vapor stream; cooling the second vapor stream in a first discharge cooler; dividing the second vapor stream into a gas product and a split stream; withdrawing the gas product; compressing, in a low-pressure compressor, the split stream; cooling the split stream in a second discharge cooler and further cooling the split stream in the heat exchanger; isentropically expanding, in a low-pressure expander, the split stream, wherein the pressure and temperature of the split stream are lowered; cooling a liquid paraffinic stream in the heat exchanger; combining the cooled liquid paraffinic stream with the expanded split stream to provide a combined feed; vaporizing the combined feed in the heat exchanger; withdrawing the vaporized combined feed; lowering the pressure of the first liquid stream in a control valve; partially vaporizing the first liquid stream in the heat exchanger; flashing the partially vaporized first liquid stream in a liquid product drum to provide a hydrogen-rich gas, which travels to a rectifier connected to the liquid product drum; combining the hydrogen-rich gas and the second liquid stream in the rectifier, further purifying the hydrogen-rich gas; warming the hydrogen-rich gas from the rectifier in the heat exchanger to provide a flashed vapor stream; pumping a third liquid stream from the liquid product drum to the heat exchanger, wherein it is warmed; and providing a liquid product.

One or more specific embodiments disclosed herein includes a process for the separation of hydrogen from an olefin hydrocarbon rich compressed effluent vapor stream from a dehydrogenation unit, comprising separating hydrogen from olefin and heavy paraffinic components in the compressed effluent vapor stream to provide a first vapor stream and a first liquid stream; separating hydrogen from olefin and heavy paraffinic components in the first vapor stream to provide a second vapor stream and a second liquid stream; expanding and compressing the second vapor stream; dividing the second vapor stream into a gas product and a split stream; compressing and expanding the split stream; lowering the pressure of the first liquid stream; partially vaporizing the first liquid stream; flashing the partially vaporized first liquid stream in a liquid product drum to provide a hydrogen-rich gas; and combining the hydrogen-rich gas and the second liquid stream in a rectifier.

One or more specific embodiments disclosed herein includes a process for the separation of hydrogen from an olefin hydrocarbon rich compressed effluent vapor stream from a dehydrogenation unit, comprising separating hydrogen from olefin and heavy paraffinic components in the compressed effluent vapor stream to provide a first vapor stream and a first liquid stream; separating hydrogen from olefin and heavy paraffinic components in the first vapor stream to provide a second vapor stream and a second liquid stream; isentropically expanding, in a high-pressure expander, the second vapor stream; compressing, in a high-pressure compressor, the second vapor stream; dividing the second vapor stream into a gas product and a split stream; compressing, in a low-pressure compressor, the split stream; and isentropically expanding, in a low-pressure expander, the split stream.

One or more specific embodiments disclosed herein includes a process for the separation of hydrogen from an olefin hydrocarbon rich compressed effluent vapor stream from a dehydrogenation unit, comprising cooling the compressed effluent vapor stream in a heat exchanger; separating hydrogen from olefin and heavy paraffinic components in the cooled compressed effluent vapor stream to provide a first vapor stream and a first liquid stream; cooling the first vapor stream in the heat exchanger; separating hydrogen from olefin and heavy paraffinic components in the cooled first vapor stream to provide a second vapor stream and a second liquid stream; warming the second vapor stream in the heat exchanger; expanding the second vapor stream; warming the second vapor stream in the heat exchanger; compressing the second vapor stream; dividing the second vapor stream into a gas product and a split stream; compressing the split stream; cooling the split stream in the heat exchanger; expanding the split stream; cooling a liquid paraffinic stream in the heat exchanger; combining the cooled liquid paraffinic stream with the expanded split stream to provide a combined feed; vaporizing the combined feed in the heat exchanger; partially vaporizing the first liquid stream in the heat exchanger; flashing the partially vaporized first liquid stream in a liquid product drum to provide a hydrogen-rich gas; warming the hydrogen-rich gas in the heat exchanger to provide a flashed vapor stream; and pumping a third liquid stream from the liquid product drum to the heat exchanger, wherein it is warmed.

In any one of the processes or systems disclosed herein, the heat exchanger may be a single heat exchanger.

In any one of the processes or systems disclosed herein, the heat exchanger may be comprised of one or more brazed aluminum heat exchanger cores.

In any one of the processes or systems disclosed herein, the compressed effluent vapor stream may be comprised of hydrogen, paraffinic hydrocarbons, and propylene or isobutylene.

In any one of the processes or systems disclosed herein, the compressed effluent vapor stream may be comprised of hydrogen, paraffinic hydrocarbons, and a mixture of propylene and isobutylene.

In any one of the processes or systems disclosed herein, the liquid paraffinic stream may be comprised of either propane, isobutane, or a combination of propane and isobutane.

In any one of the processes or systems disclosed herein, the process may be performed without the employment of external refrigeration.

In any one of the processes or systems disclosed herein, a booster compressor may be employed to provide additional pressure to the second vapor stream from the high-pressure compressor.

In any one of the processes or systems disclosed herein, the high-pressure expander, the low-pressure expander, the high-pressure compressor, and the low-pressure expander may be mounted to a bull gear.

In any one of the processes or systems disclosed herein, a motor may be employed to drive the bull gear.

In any one of the processes or systems disclosed herein, one or more electric generators may be driven by the power produced in the high-pressure expander, low-pressure expander, or both expanders.

In any one of the processes or systems disclosed herein, the high-pressure expander and the low-pressure expander may be configured in series.

In any one of the processes or systems disclosed herein, the high-pressure compressor and the low-pressure compressor may be configured into two or more stages in series.

In any one of the processes or systems disclosed herein, the high-pressure compressor may be driven by the power produced in the high-pressure expander.

In any one of the processes or systems disclosed herein, the low-pressure compressor may be driven by the power produced in the low-pressure expander.

In any one of the processes or systems disclosed herein, a coldbox may be employed to contain all low-temperature and cryogenic equipment and parts.

In any one of the processes or systems disclosed herein, the withdrawn combined feed may be employed as a feed stream to a dehydrogenation reactor.

In any one of the processes or systems disclosed herein, the withdrawn liquid product may be introduced into a product storage system.

In any one of the processes or systems disclosed herein, the flashed vapor stream may be recycled to a feed compressor.

In any one of the processes or systems disclosed herein, the liquid product drum may be maintained at a temperature such that the liquid product drum may be composed of carbon steel.

In any one of the processes or systems disclosed herein, the composition and mass flow of the second vapor stream to the high-pressure expander and the high-pressure compressor may remain substantially unchanged.

In any one of the processes or systems disclosed herein, the composition and mass flow of the split stream to the low-pressure expander and the low-pressure compressor may remain substantially unchanged.

In any one of the processes or systems disclosed herein, the high-pressure expander and high-pressure compressor set and the low-pressure expander and low-pressure compressor set may be magnetic bearing type expander/compressor sets.

In any one of the processes or systems disclosed herein, the high-pressure expander and high-pressure compressor set and the low-pressure expander and low-pressure compressor set may be oil bearing type sets that share a common lube oil system.

One or more specific embodiments disclosed herein includes a separation system which utilizes a process for the separation of hydrogen from an olefin hydrocarbon rich compressed effluent vapor stream from a dehydrogenation unit comprising a heat exchanger for cooling the compressed effluent vapor stream, cooling the first vapor product, warming the second vapor product, reheating the second vapor product, cooling the split stream, cooling a liquid paraffinic feed for use in the reactor, vaporizing the combined stream, partially vaporizing the first liquid product, warming the hydrogen-rich gas from the rectifier, and warming the flashed liquid stream from the liquid product drum; a first separator in which the cooled compressed effluent vapor stream is separated to provide a first vapor product and a first liquid product; a second separator in which the cooled first vapor product is separated to provide a second vapor product and a second liquid product; a high-pressure expander for isentropically expanding the second vapor product; a high-pressure compressor for compressing the second vapor product; a low-pressure compressor for compressing the split stream; a low-pressure expander for isentropically expanding the split stream; a rectifier for flashing the partially vaporized first liquid product to provide a hydrogen-rich gas and combining the hydrogen-rich gas with the second liquid product.

4. Specific Embodiments in the Figures

The drawings presented herein are for illustrative purposes only and are not intended to limit the scope of the claims. Rather, the drawings are intended to help enable one having ordinary skill in the art to make and use the claimed inventions.

Figure 2:
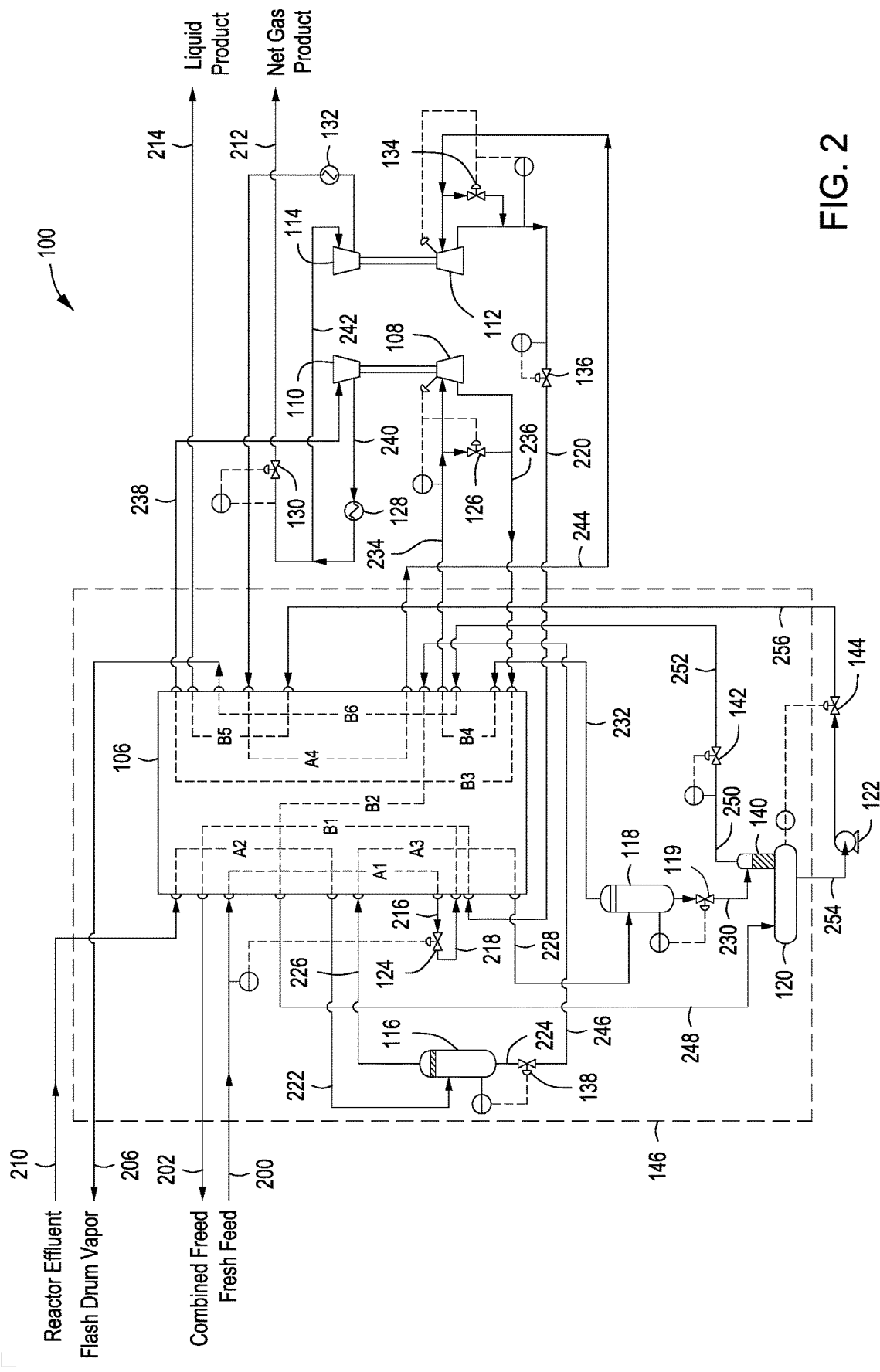
FIG. 2 is a schematic illustration, flow diagram of a system for hydrogen separation.
Figure 3:
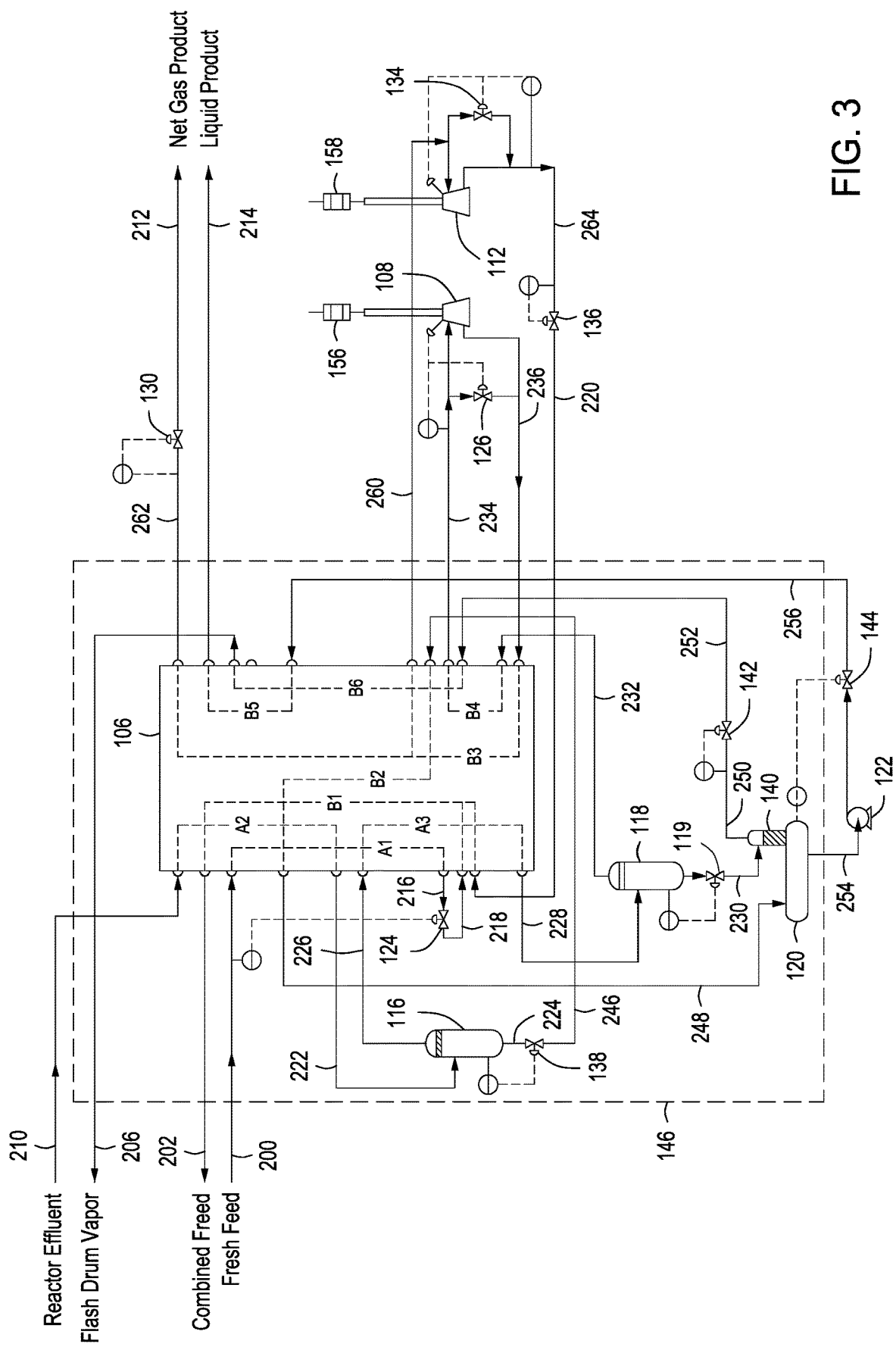
FIG. 3 is a schematic illustration, flow diagram of FIG. 2, but showing the optional use of an expander/electric generator system.

Referring to FIGS. 1-3, a specific embodiment, e.g., version or example, of a system for hydrogen separation from an olefin hydrocarbon rich compressed effluent vapor stream is illustrated. These figures may show features which may be found in various specific embodiments, including the embodiments shown in this specification and those not shown.

FIG. 1 shows a system for hydrogen separation, processing unit 100, with a dehydrogenation unit 102 and a reactor effluent compressor unit 104. A fresh feed 200 is a liquid paraffinic stream mainly composed of propane, isobutane, or a mixture of propane and isobutane. Fresh feed 200 is mixed with a recycle gas 220 (not shown), which is produced within the processing unit 100. Recycle gas 220 contains primarily hydrogen. The combination of fresh feed 200 and recycle gas 220 is vaporized within the processing unit 100 and emerges as a combined feed 202. The combined feed 202 enters the dehydrogenation unit 102, where the combined feed 202 is dehydrogenated resulting in an effluent gas stream 204. Effluent gas stream 204 is a low-pressure effluent stream composed of hydrogen, olefins, and other hydrocarbons. Effluent gas stream 204 is then mixed with a flash drum vapor 206, which is primarily hydrogen, to form a feed gas stream 208. The feed gas stream 208 enters the reactor effluent compressor unit 104, where the feed gas stream 208 has its pressure increased and then its temperature lowered before entering processing unit 100. A reactor effluent 210 exits the reactor effluent compressor unit 104 containing a mixture of hydrogen and hydrocarbons. There are two product streams produced from the processing unit 100. One is a hydrogen-rich gas product stream, referred to as a net gas product 212, and the other is an olefin-rich liquid product stream, referred to as a liquid product 214, which has a boosted pressure.

The processing unit 100 is a system design and flow system that can be connected to a propane dehydrogenation (PDH) unit, an isobutane dehydrogenation (BDH) unit, or a propane/isobutane dehydrogenation (PBDH) unit for hydrogen separation from the reactor effluent. The process conditions (temperature, pressure, composition) are different for PDH, BDH, and PBDH, but the basic process flow scheme may be the same. Illustrative process conditions at key points are listed in the tables below.

TABLE 1

An Example of Process Conditions of the Key Streams for a PDH Plant

| | | Stream No. | | | | | | |
|---|---|---|---|---|---|---|---|---|
| | | 200 | 202 | 204 | 206 | 210 | 214 | 212 |
| | | Stream Name | | | | | | |
| | | Fresh Feed | Combined Feed | Effluent Gas Stream | Flash Drum Vapor | Reactor Effluent | Liquid Product | Net Gas Product |
| Pressure | kPa · G | 2200 | 350 | 5 | 5 | 1190 | 4000 | 590 |
| Temperature | ° C. | 52 | 37 | 43 | 37 | 43 | 49 | 43 |
| Hydrogen | Mole % | 0.0000 | H2/HCBN | 45.6105 | 70.9685 | 45.6936 | 0.0545 | 95.6074 |
| Methane | Mole % | 0.0000 | Ratio: | 2.6676 | 24.9248 | 2.7406 | 1.3315 | 4.1340 |
| Ethylene | Mole % | 0.0000 | 0.42-0.5 | 0.1062 | 0.1596 | 0.1064 | 0.1820 | 0.0230 |
| Ethane | Mole % | 0.7089 | | 2.0304 | 1.3530 | 2.0282 | 3.7273 | 0.1681 |
| Propylene | Mole % | 0.7793 | | 15.9163 | 1.0486 | 15.8676 | 30.3881 | 0.0339 |
| Propane | Mole % | 98.3613 | | 33.5518 | 1.5445 | 33.4469 | 64.0928 | 0.0336 |
| Propadiene | Mole % | 0.0000 | | 0.0024 | 0.0001 | 0.0024 | 0.0047 | 0.0000 |
| Methyl acetylene | Mole % | 0.0000 | | 0.0103 | 0.0004 | 0.0102 | 0.0196 | 0.0000 |
| Isobutane | Mole % | 0.1407 | | 0.0472 | 0.0003 | 0.0470 | 0.0902 | 0.0000 |
| Isobutylene | Mole % | 0.0065 | | 0.0263 | 0.0001 | 0.0262 | 0.0503 | 0.0000 |
| 1-butene | Mole % | 0.0000 | | 0.0006 | 0.0000 | 0.0006 | 0.0011 | 0.0000 |
| Normal butane | Mole % | 0.0034 | | 0.0002 | 0.0000 | 0.0002 | 0.0004 | 0.0000 |
| Cis-2-butene | Mole % | 0.0000 | | 0.0006 | 0.0000 | 0.0006 | 0.0011 | 0.0000 |
| Trans-2-butene | Mole % | 0.0000 | | 0.0007 | 0.0000 | 0.0007 | 0.0013 | 0.0000 |
| Benzene | Mole % | 0.0000 | | 0.0254 | 0.0000 | 0.0253 | 0.0485 | 0.0000 |
| Toluene | Mole % | 0.0000 | | 0.0034 | 0.0000 | 0.0034 | 0.0065 | 0.0000 |
| Xylene (as p-xylene) | Mole % | 0.0000 | | 0.0000 | 0.0000 | 0.0000 | 0.0000 | 0.0000 |
| Heavy hydrocarbons (as anthracene) | Mole % | 0.0000 | | 0.0000 | 0.0000 | 0.0000 | 0.0000 | 0.0000 |

Notes:
1. Liquid product 214 to have >99.9% C3 Recovery
2. Net gas product 212 to have Minimum H2 >92.5%; Max Total Olefins <0.1%; C3+ Olefins, <0.05%

TABLE 2

An Example of Process Conditions of the Key Streams for a BDH Plant

| | | Stream No. | | | | | | |
|---|---|---|---|---|---|---|---|---|
| | | 200 | 202 | 204 | 206 | 210 | 214 | 212 |
| | | Stream Name | | | | | | |
| | | Fresh Feed | Combined Feed | Effluent Gas Stream | Flash Drum Vapor | Reactor Effluent | Liquid Product | Net Gas Product |
| Pressure | kPa · G | 783 | 350 | 7 | 7 | 599 | 906 | 481 |
| Temperature | ° C. | 49 | 37 | 43 | 35 | 39 | 47 | 39 |
| Hydrogen | Mole % | 0.0000 | H2/HCBN | 47.8013 | 72.8813 | 47.8426 | 0.0525 | 93.9978 |
| Methane | Mole % | 0.0000 | Ratio: | 2.8804 | 19.7952 | 2.9081 | 0.4244 | 5.2564 |
| Ethylene | Mole % | 0.0000 | 0.3-0.4 | 0.0041 | 0.0185 | 0.0041 | 0.0038 | 0.0043 |
| Ethane | Mole % | 0.0000 | | 0.1536 | 0.4872 | 0.1541 | 0.1980 | 0.1106 |
| Propylene | Mole % | 0.0000 | | 0.4072 | 0.2578 | 0.4069 | 0.7790 | 0.0474 |
| Propane | Mole % | 0.7046 | | 1.4840 | 0.8252 | 1.4829 | 2.8683 | 0.1446 |

TABLE 2-continued

An Example of Process Conditions of the Key Streams for a BDH Plant

| | | Stream No. | | | | | | |
|---|---|---|---|---|---|---|---|---|
| | | 200 | 202 | 204 | 206 | 210 | 214 | 212 |
| | | Stream Name | | | | | | |
| | | Fresh Feed | Combined Feed | Effluent Gas Stream | Flash Drum Vapor | Reactor Effluent | Liquid Product | Net Gas Product |
| Propadiene | Mole % | 0.0000 | | 0.0000 | 0.0000 | 0.0000 | 0.0000 | 0.0000 |
| Methyl acetylene | Mole % | 0.0000 | | 0.0001 | 0.0000 | 0.0001 | 0.0002 | 0.0000 |
| Isobutane | Mole % | 97.5005 | | 26.1652 | 3.5254 | 26.1280 | 52.9086 | 0.2912 |
| Isobutylene | Mole % | 0.0018 | | 20.0619 | 2.1378 | 20.0324 | 40.6490 | 0.1441 |
| 1-butene | Mole % | 0.0000 | | 0.1178 | 0.0116 | 0.1177 | 0.2389 | 0.0007 |
| Normal butane | Mole % | 1.7931 | | 0.5800 | 0.0408 | 0.5792 | 1.1776 | 0.0019 |
| Cis-2-butene | Mole % | 0.0000 | | 0.1308 | 0.0075 | 0.1306 | 0.2657 | 0.0003 |
| Trans-2-butene | Mole % | 0.0000 | | 0.1875 | 0.0117 | 0.1872 | 0.3808 | 0.0005 |
| Benzene | Mole % | 0.0000 | | 0.0044 | 0.0000 | 0.0044 | 0.0089 | 0.0000 |
| Toluene | Mole % | 0.0000 | | 0.0044 | 0.0000 | 0.0044 | 0.0089 | 0.0000 |
| Xylene (as p-xylene) | Mole % | 0.0000 | | 0.0174 | 0.0000 | 0.0174 | 0.0355 | 0.0000 |
| Heavy hydrocarbons (as anthracene) | Mole % | 0.0000 | | 0.0000 | 0.0000 | 0.0000 | 0.0000 | 0.0000 |

Notes:
1. Liquid product 214 to have >90% C4 Recovery
2. Net gas product 212 to have Minimum H2 >90%; Max C4+ Olefins <0.03%

TABLE 3

An Example of Process Conditions of the Key Streams for a PBDH Plant

| | | Stream No. | | | | | | |
|---|---|---|---|---|---|---|---|---|
| | | 200 | 202 | 204 | 206 | 210 | 214 | 212 |
| | | Stream Name | | | | | | |
| | | Fresh Feed | Combined Feed | Effluent Gas Stream | Flash Drum Vapor | Reactor Effluent | Liquid Product | Net Gas Product |
| Pressure | kPa · G | 1830 | 260 | 5 | 5 | 1070 | 4240 | 505 |
| Temperature | °C. | 37 | 48 | 43 | 48 | 51 | 35 | 43 |
| Hydrogen | Mole % | 0.0000 | H2/HCBN Ratio: 0.3-0.4 | 45.9920 | 79.7057 | 46.0635 | 0.0497 | 96.6271 |
| Methane | Mole % | 0.0000 | | 2.1818 | 18.8848 | 2.2172 | 1.1821 | 3.2835 |
| Ethylene | Mole % | 0.0000 | | 0.0159 | 0.0192 | 0.0159 | 0.0274 | 0.0031 |
| Ethane | Mole % | 0.0013 | | 0.6943 | 0.3576 | 0.6936 | 1.2766 | 0.0526 |
| Propylene | Mole % | 0.4579 | | 6.1041 | 0.2484 | 6.0917 | 11.6320 | 0.0115 |
| Propane | Mole % | 56.0496 | | 23.3764 | 0.7083 | 23.3283 | 44.5664 | 0.0219 |
| Propadiene | Mole % | 0.0000 | | 0.0004 | 0.0000 | 0.0004 | 0.0008 | 0.0000 |
| Methyl acetylene | Mole % | 0.0000 | | 0.0017 | 0.0000 | 0.0017 | 0.0033 | 0.0000 |
| Isobutane | Mole % | 42.6054 | | 11.4073 | 0.0468 | 11.3832 | 21.7572 | 0.0001 |
| Isobutylene | Mole % | 0.0207 | | 9.5945 | 0.0280 | 9.5742 | 18.2998 | 0.0001 |
| 1-butene | Mole % | 0.0000 | | 0.0739 | 0.0002 | 0.0737 | 0.1409 | 0.0000 |
| Normal butane | Mole % | 0.8652 | | 0.3381 | 0.0006 | 0.3374 | 0.6449 | 0.0000 |
| Cis-2-butene | Mole % | 0.0000 | | 0.0806 | 0.0001 | 0.0804 | 0.1537 | 0.0000 |
| Trans-2-butene | Mole % | 0.0000 | | 0.1165 | 0.0002 | 0.1163 | 0.2223 | 0.0000 |
| Benzene | Mole % | 0.0000 | | 0.0089 | 0.0000 | 0.0089 | 0.0169 | 0.0000 |
| Toluene | Mole % | 0.0000 | | 0.0022 | 0.0000 | 0.0022 | 0.0041 | 0.0000 |
| Xylene (as p-xylene) | Mole % | 0.0000 | | 0.0095 | 0.0000 | 0.0095 | 0.0182 | 0.0000 |
| Heavy hydrocarbons (as anthracene) | Mole % | 0.0000 | | 0.0019 | 0.0000 | 0.0019 | 0.0037 | 0.0000 |

Notes:
1. Liquid product 214 to have >95% C3 Recovery
2. Net gas product 212 to have Minimum H2 >95%; Max Total Olefins <0.1%; Max C3+ Olefins <0.05%

FIG. 2 shows the detailed configuration of the processing unit 100 with an integrated main heat exchanger 106, two separate expander/compressor sets (108/110 and 112/114), a first stage cold gas-liquid separator 116, a second stage cold gas-liquid separator 118, a liquid product drum 120, and a liquid product pump 122. Based on different process conditions, the integrated main heat exchanger 106 may, in the alternative, be configured into two or more heat exchangers in series or parallel.

The two separate expander/compressor sets (108/110 and 112/114) may be two independent magnetic-bearing type or two sets of oil-bearing type that share a common lube oil system. Each expander/compressor set (108/110 and 112/114) may be configured into two or more stages in series setup depending on the pressure ratios of the expansion and compression, the flow rates, and other factors.

Fresh feed 200 enters warm pass A1 at the upper warm end of the integrated main heat exchanger 106 where the fresh feed 200 is cooled to a low temperature and exits pass A1 at the lower cold end of the integrated main heat exchanger 106 as an outlet stream 216. The pressure of the outlet stream 216 is then reduced by a flow control valve 124 to a pressure that meets the required pressure of combined feed 202, which feeds the dehydrogenation unit 102 (not shown).

Outlet stream 218 of flow control valve 124 then returns to the integrated main heat exchanger 106 via pass B1 where it mixes with recycle gas 220 from the discharge of the low-pressure expander 112. The mixed stream of recycle gas 220 and outlet stream 218 travels upward along the channel of pass B1, where heat exchanging occurs between the cold stream pass B1 and warm stream passes A1, A2, A3, and A4. Before exiting through pass B1, the mixed stream is completely vaporized and becomes a superheated vapor stream. The superheated vapor stream is referred to as combined feed 202 after exiting pass B1. The pressure of combined feed 202 is maintained at a constant value by the feed of the dehydrogenation unit 102 (not shown). The combined feed 202 is the reactor feedstock for dehydrogenation unit 102 (not shown).

The reactor effluent 210, an olefin-hydrogen effluent stream from the reactor effluent compressor unit 104 (not shown), enters pass A2 at the upper warm end of the integrated main heat exchanger 106, where the stream is cooled to a low temperature as it flows through and exits pass A2 in the middle of the integrated main heat exchanger 106. The cooling of the reactor effluent 210 as it travels through pass A2 is caused by cold stream passes B1 through B6. Outlet stream 222 from pass A2 enters the first stage cold gas-liquid separator 116 with a low temperature, at which time a majority, >95%, of the olefin and heavy paraffinic components in outlet stream 222 are condensed to liquid, which is separated out as liquid stream 224. Further, almost all, >99% of the hydrogen from outlet stream 222 remains vapor, and the first stage cold gas-liquid separator 116 separates out the vapor as vapor stream 226.

The vapor stream 226 then flows back to the integrated main heat exchanger 106 through pass A3, where it is cooled to a lower temperature by the time it exits pass A3 at the lower end of the integrated main heat exchanger 106. The outlet stream 228 from pass A3 enters the second stage cold gas-liquid separator 118, where almost all, >85%, of the olefin and heavy paraffinic components in outlet stream 228 are condensed to liquid stream 230 and almost all, >99.95% of the hydrogen stays in vapor stream 232. The vapor stream 232 exits second stage cold gas-liquid separator 118 and returns to the integrated main heat exchanger 106 through pass B4, where vapor stream 232 is warmed before exiting pass B4 of the integrated main heat exchanger 106 as outlet stream 234. Outlet stream 234 is superheated and enters the high-pressure expander 108, where it is expanded by "isentropic" gas expansion process to a lower pressure and lower temperature to become a cold stream 236. The output power from the high-pressure expander 108 drives high-pressure compressor 110. The high-pressure expander 108 is equipped with an IGV (inlet guide vane) and bypass control valve 126 to maintain a constant pressure at the inlet of high-pressure expander 108.

Cold stream 236 may or may not contain liquid. Cold stream 236 flows directly into pass B3 at the lower cold end of the integrated main heat exchanger 106 and travels up pass B3, where it exchanges heat with warm stream passes A1, A2, A3, and A4. As cold stream 236 travels through pass B3, it is warmed to a temperature close to the inlet temperatures of passes A1, A2, A3, and A4 by the time it exits pass B3 at the upper warm end of the integrated main heat exchanger 106. An outlet stream 238 from pass B3 then flows to high-pressure compressor 110, where the pressure of outlet stream 238 is increased to meet the pressure requirement of the net gas product 212. A discharge stream 240 from high-pressure compressor 110, which contains primarily hydrogen and other lighter hydrocarbons (e.g. methane and ethane) from the reactor effluent 210, is cooled down by a high-pressure compressor discharge cooler 128 before being split into two streams. One stream is the net gas product 212, which is sent to a downstream production facility. The pressure of the net gas product 212 determines the discharge pressure of the high-pressure compressor 110. A pressure control valve 130 maintains a minimum required discharge pressure of the high-pressure compressor 110 to protect the high-pressure compressor 110 in case the pressure of the net gas product 212 is lost.

The second stream from the discharge of the high-pressure compressor discharge cooler 128 is a split stream 242. Split stream 242 is routed to the low-pressure compressor 114 where its pressure is boosted. Split stream 242 is then cooled by a low-pressure compressor discharge cooler 132, before entering warm stream pass A4 at the upper warm end of the integrated main heat exchanger 106. Split stream 242 is cooled to a low temperature as it flows down and exits pass A4 at the middle of the integrated main heat exchanger 106. An outlet stream 244 of pass A4 then flows back to the low-pressure expander 112, where it is expanded to a lower pressure and lower temperature through "isentropic" gas expansion process. The output power from the low-pressure expander 112 drives low-pressure compressor 114. The low-pressure expander 112 discharge stream is recycle gas 220 that mixes with outlet stream 218 to become combined feed 202.

The low-pressure expander 112 is equipped with an IGV (inlet guide vane) and bypass control valve 134 to maintain a constant flow for recycle gas 220 to mix with outlet stream 218 in order to meet the $H_2$/hydrocarbon mole ratio specified for combined feed 202. The $H_2$/hydrocarbon mole ratio is defined as (moles of hydrogen in combined feed 202)/(moles of hydrocarbon in combined feed 202). This ratio is typically specified by the license of dehydrogenation reactors, for example the UOP's OLEFLEX™ dehydrogenation reactor.

The pressure of combined feed 202 determines the discharge pressure of the low-pressure expander 112. A pressure control valve 136 maintains a minimum required pressure of the low-pressure expander 112 to protect the low-pressure expander 112 from "flying out" in case the pressure of the combined feed 202 is lost.

Returning to the first stage cold gas-liquid separator 116, the pressure of the olefin-rich liquid stream 224 is reduced by level control valve 138 before it enters pass B2 of the integrated main heat exchanger 106 as cold stream 246. Cold stream 246 enters pass B2 at the lower cold end of the integrated main heat exchanger 106 where cold stream 246 exchanges heat with the warm passes A1, A2, and A4 and becomes partially vaporized. This partially vaporized stream 248 exits pass B2 in the middle of the integrated main heat exchanger 106 and flows to the liquid product drum 122. Once in the liquid product drum 120, light components, mainly hydrogen, methane, ethane, and maybe some C3+ components, flash out from the liquid and travel upward through the rectifier 140 located on the top of the liquid product drum 120. The upward travelling hydrogen-rich gas in the rectifier 140, which is a packed column, makes contact with the downward travelling colder liquid stream 230 from the second stage cold gas-liquid separator 118. Heat and mass transferring occurs in the rectifier 140, and therefore the hydrogen-rich gas in the rectifier 140 is further purified to meet the minimum hydrogen content specification of the flash drum vapor 206, before exiting the top of the rectifier 140 as a vapor stream 250.

The pressure of the liquid product drum 120 is maintained by a pressure control valve 142 on vapor stream 250 to a constant pressure to maximize the recovery of olefin and heavy hydrocarbon components in the liquid product 214 and to meet the specification of the maximum allowable hydrogen content in the liquid product 214.

After the pressure control valve 142, a cold stream 252 contains certain olefin components in addition to the main light components hydrogen, methane, and ethane. The cold stream 252 enters cold stream pass B6 at the lower cold end of the integrated main heat exchanger 106. As cold stream 252 travels up pass B6, it exchanges heat with the warm stream passes A1, A2, A3, and A4, and cold stream 252 is warmed to a temperature close to the inlet temperature of reactor effluent 210 or fresh feed 200 as it exits pass B6. The flash drum vapor 206 from pass B6 then flows back to the inlet of the reactor effluent compressor unit 104 (not shown).

The separated cold liquid stream 254 from the liquid product drum 120 is pumped by the liquid product pump 122 to a pressure that meets the required pressure of the liquid product 214. The liquid level of the liquid product drum 120 is maintained by a level control valve 144.

The cold liquid product stream 256 then enters pass B5 at the middle of the integrated main heat exchanger 106. As the liquid product stream 256 travels upward in pass B5, it exchanges heat with the warm passes A1, A2, and A4 and is warmed to a temperature defined by the liquid product 214 specification as it exits pass B5 at the upper warm end of the integrated main heat exchanger 106. The liquid product 214 is then sent to a production facility.

The liquid product drum 120 may be maintained at a temperature greater than −15° C., and therefore, liquid product drum 120 and liquid product pump 122 may be constructed of carbon steel for additional cost savings.

Liquid product drum 120 is elevated to a height to get enough NPSHa (net positive suction head available) for the liquid product pump 122 to avoid cavitation damage to the liquid product pump 122.

Further, a coldbox 146 is designed to contain all low-temperature equipment including the integrated main heat exchanger 106, the first stage cold gas-liquid separator 116, the second stage cold gas-liquid separator 118, and the liquid product drum 120, as well as the associated piping. Control valves 138, 119, 142, and 124 can either be enclosed within or installed outside of the coldbox 146. The coldbox 146 is typically filled with insulation material and purged with nitrogen to provide cold insulation for the low-temperature equipment and parts.

Figure 2A:
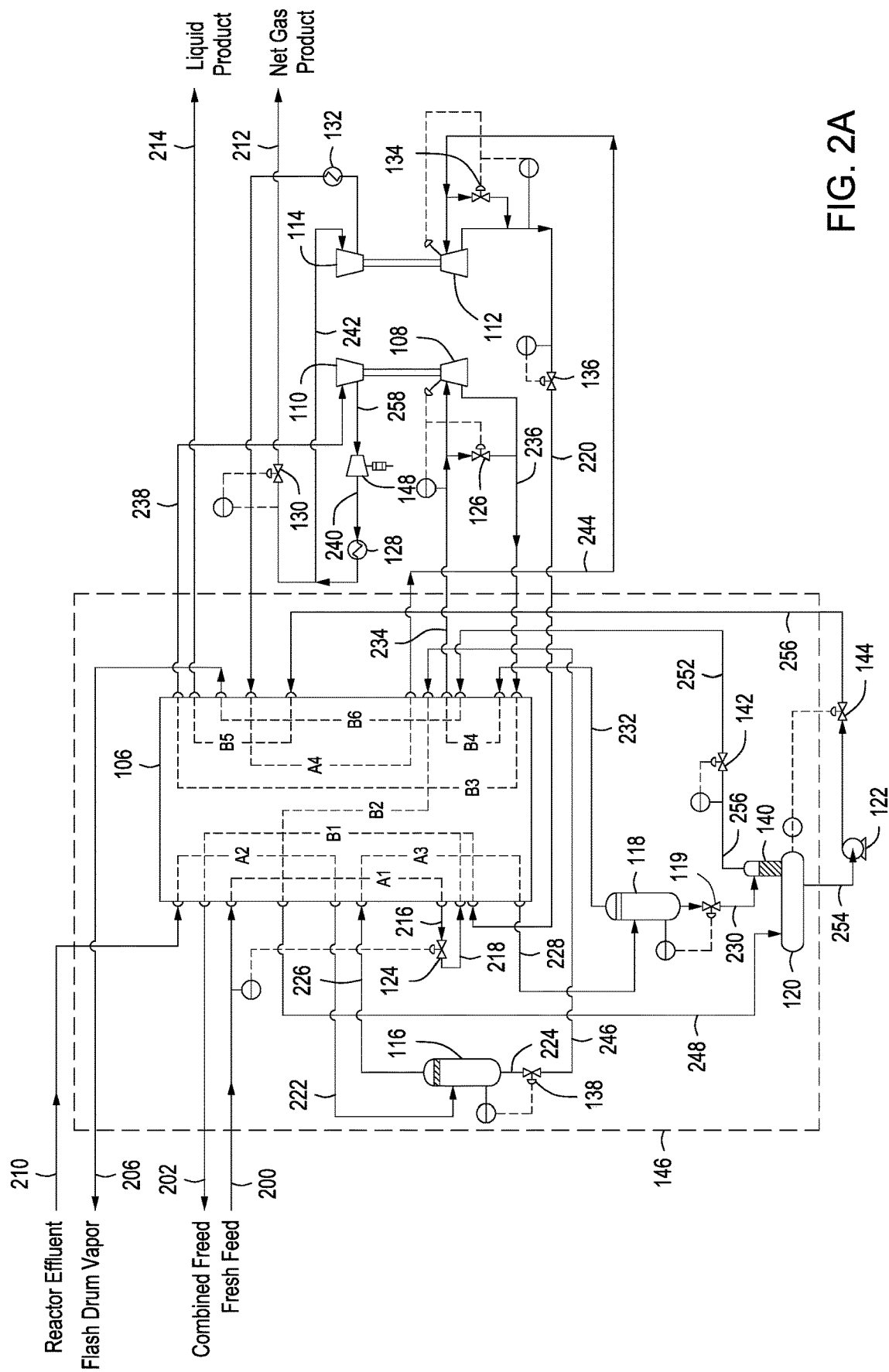
FIG. 2A is a portion of the schematic illustration, flow diagram of FIG. 2, but showing the optional use of a booster compressor.

FIG. 2A shows the option of two separate expander/compressor sets (108/110 and 112/114) with an additional booster compressor 148 located at the discharge of the high-pressure compressor 110. The only difference between FIG. 2 and FIG. 2A is the addition of the booster compressor 148, which is used to provide additional pressure to discharge stream 258 from high-pressure compressor 110. Further, booster compressor 148 achieves the required refrigeration for the effluent gas stream 204, especially when the pressure difference between the reactor effluent 210 and the net gas product 212 is not high enough to achieve the required refrigeration. The booster compressor 148 is an independent compressor driven by either electrical motor or other type of driver.

Figure 2B:
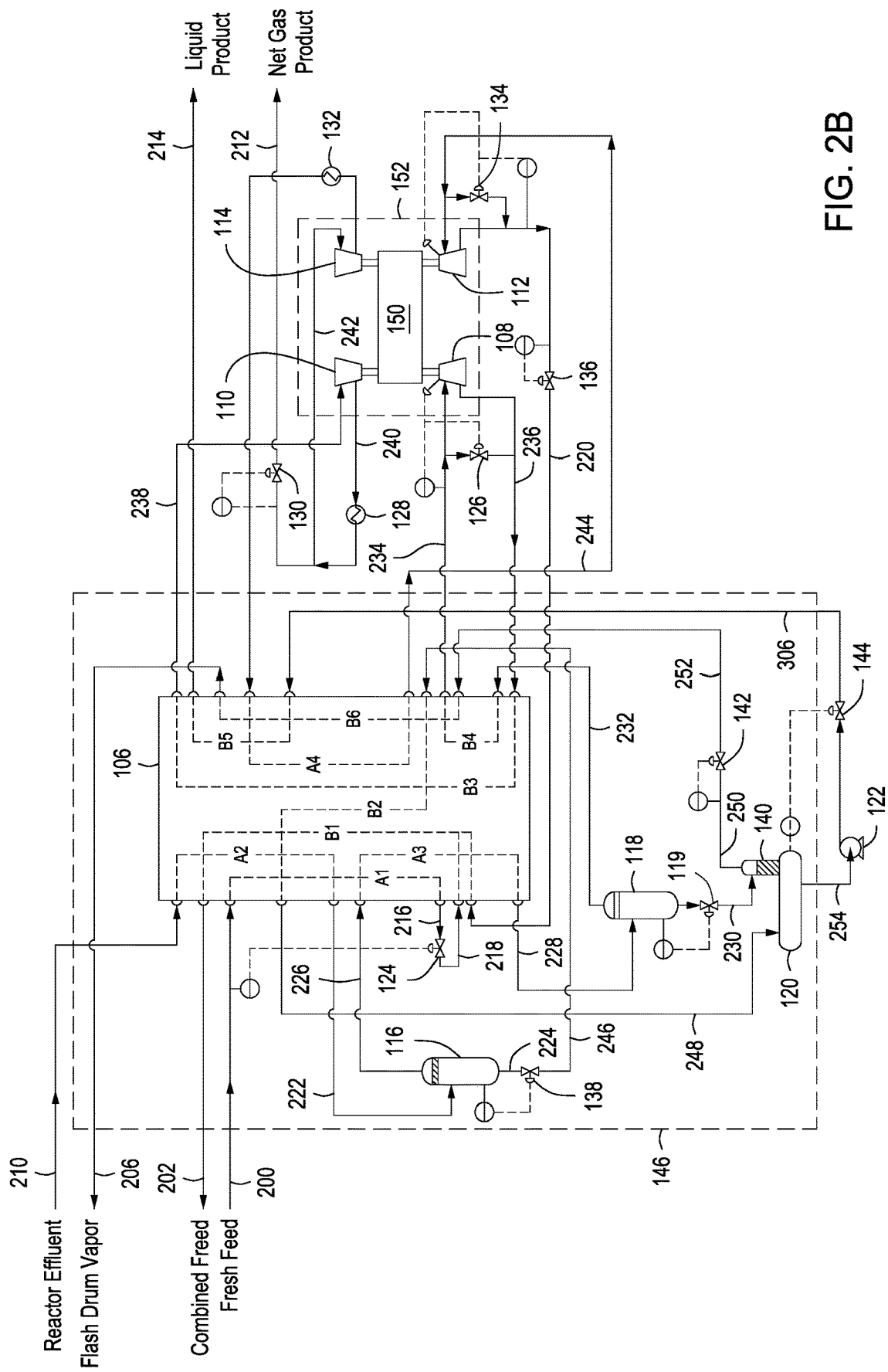
FIG. 2B is a portion of the schematic illustration, flow diagram of FIG. 2, but showing the optional use of a non-driver I-Compander.

FIG. 2B shows the non-driver I-Compander option. The only difference between FIG. 2 and FIG. 2B is that the high-pressure expander 108, the low-pressure expander 112, the high-pressure compressor 110, and the low-pressure compressor 114 are mounted to a common bull gear 150 to form a so called non-driver I-Compander 152. Depending on the pressure ratios of expansion, flow rate, and other factors, each expander may also be set up in series with multiple stages available. Each compressor can be configured into two or more stages in serial setup depending on the pressure ratios of the compression, the flow rate, and other factors.

Figure 2C:
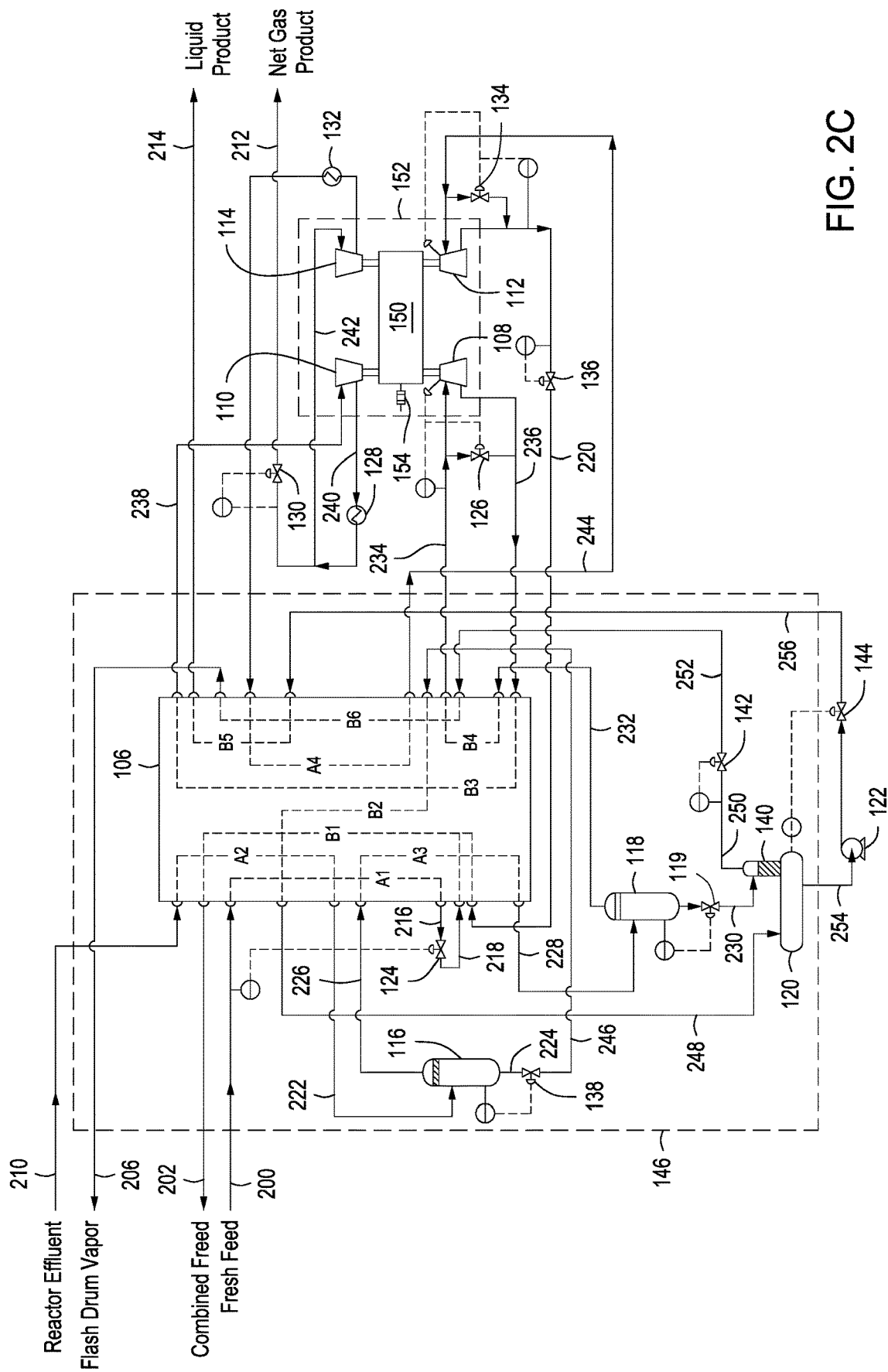
FIG. 2C is the schematic illustration, flow diagram of FIG. 2B, but showing the optional use of a motor-driver I-Compander.

FIG. 2C shows the motor-driver I-Compander option. The only difference between FIG. 2B and FIG. 2C is the addition of a motor driver, electric motor 154, to the bull gear 150 of the I-Compander 152. The power that drives the compressor(s) is from the high-pressure expander—108 and the low-pressure expander 112, with additional power input from the electric motor 154. The only difference between the "motor-driver option" and the "non-driver option" is the addition of the electric motor 154 that provides additional power for the compressor(s) to boost the pressure of discharge stream 240 and the pressure of outlet stream 244 high enough to provide the required refrigeration. The power input to the I-Compander 152 by the electric motor 154 is needed especially when the pressure difference between the reactor effluent 210 and the net gas product 212 is not high enough to achieve the required refrigeration.

FIG. 3 shows the expander/electric-generator option of the processing unit 100 in FIG. 1. It illustrates configuration of the integrated main heat exchanger 106, two separate expander/electric-generator sets (108/156 and 112/158), the first stage cold gas-liquid separator 116, the second stage cold gas-liquid separator 118, the liquid product drum 120 and the liquid product pump 122. The differences between FIG. 3 and FIG. 2 include the configurations of the expander sets as well as the details identified below.

Stream 234 exits pass B4 of the integrated main heat exchanger 106 superheated and enters the high-pressure expander 108, where stream 234 is expanded to a lower pressure and lower temperature through a so-called "isentropic" gas expansion process. The output power from the high-pressure expander 108 drives electric generator 156 to produce electricity. The high-pressure expander 108 is equipped with an IGV (inlet guide vanes) and bypass control valve 126 to maintain a constant pressure at the expander inlet.

The cold outlet stream 236 from the high-pressure expander 108 may or may not contain liquid. It flows directly into pass B3 located at the lower cold end of the integrated main heat exchanger 106 and travels up in pass B3, where cold outlet stream 236 exchanges heat with the warm stream passes A1, A2, and A3. A side stream 260 is taken out from the middle of pass B3 as feed to the low-pressure expander 112.

The outlet stream 262 of pass B3 flows through pressure control valve 130 as net gas product 212 to a downstream production facility. The pressure of the net gas product 212 determines the discharge pressure of the high-pressure expander 108. The pressure control valve 130 is to maintain a minimum required discharge pressure of the high-pressure expander 108 to protect the expander from "flying out" in case the pressure of the net gas product stream is lost.

The side-stream 260 from pass B3 is routed to the low-pressure expander 112, where it is expanded to a lower pressure and lower temperature through "isentropic" gas expansion process. The output power from the low-pressure expander 112 drives electric generator 158 to produce electricity.

The low-pressure expander 112 is equipped with an IGV (inlet guide vanes) and bypass control valve 134 to maintain a constant flow for stream 264, which is the required hydrogen-rich recycle gas flow to mix with the liquid paraffinic stream 218 to meet the H2/HCBN mole ratio specification for the combined feed 202. The H2/HCBN mole ratio is defined as (moles of hydrogen in the combined feed 202)/(moles of hydrocarbon in combined feed 202). This ratio is typically specified by the license of dehydrogenation reactors, for example the UOP's OLEFLEX™ dehydrogenation reactor.

The pressure of the combined feed 202 determines the discharge pressure of the low-pressure expander 112. A pressure control valve 136 is installed to maintain a minimum required pressure of the low-pressure expander 112 to protect the expander from "flying out" in case the pressure of the combined feed 202 is lost. The stream 220 from pressure control valve 136 commingles with stream 218 as detailed in the description of FIG. 2. The stream 220 is the recycle gas stream that mixes with stream 218 to become the combined feed 202.

Generally, the above describes an improved process and system for separation of hydrogen from an effluent by dehydrogenation of propane, isobutane, or a mixture of both. More specifically, the use of a single heat exchanger allows for a more balanced process reducing off-design, i.e. not allowed for or expected, flow distributions. This provides improved thermodynamic efficiency and stability. Further, a single heat exchanger with a compact design takes up less space, which can be a significant benefit in an industrial setting.

Further, the expander configuration with two sets of expanders/compressors improves the process. In the description above, the composition and mass flow of the stream to each set of expander/compressor remains substantially unchanged. This improves the energy benefit by recovering the expander power back to the system. Also, the hydrogen-rich gas in the rectifier is further purified to meet the minimum hydrogen content specification of the flash drum vapor, which in turn improves the $C_3$ liquid product recovery,

What is claimed is:

1. A process for the separation of hydrogen from an olefin hydrocarbon rich compressed effluent vapor stream from a dehydrogenation unit, which process comprises:
   a. introducing the compressed effluent vapor stream into a heat exchanger;
   b. cooling the compressed effluent vapor stream in the heat exchanger;
   c. separating hydrogen from olefin and heavy paraffinic components in the cooled compressed effluent vapor stream in a first separator to provide a first vapor stream and a first liquid stream;
   d. cooling the first vapor stream in the heat exchanger;
   e. separating hydrogen from olefin and heavy paraffinic components in the cooled first vapor stream in a second separator to provide a second vapor stream and a second liquid stream;
   f. warming the second vapor stream in the heat exchanger;
   g. isentropically expanding, in a first expander, the warmed second vapor stream, wherein the pressure and temperature of the warmed second vapor stream are lowered;
   h. warming the isentropically expanded second vapor stream in the heat exchanger;
   i. removing a side stream from the isentropically expanded second vapor stream;
   j. withdrawing the warmed, isentropically expanded second vapor stream from the heat exchanger;
   k. isentropically expanding, in a second expander, the side stream, wherein the pressure and temperature of the isentropically expanded side stream are lowered;
   l. cooling a liquid paraffinic stream in the heat exchanger;
   m. combining the cooled liquid paraffinic stream with the isentropically expanded side stream to provide a combined feed;
   n. vaporizing the combined feed in the heat exchanger;
   o. withdrawing the vaporized combined feed from the heat exchanger;
   p. lowering the pressure of the first liquid stream from the first separator in a control valve, wherein the temperature of the first liquid stream is reduced;
   q. partially vaporizing the cooled first liquid stream in the heat exchanger;
   r. flashing the partially vaporized first liquid stream in a liquid product drum to provide a hydrogen-rich gas, wherein the hydrogen-rich gas travels to a rectifier connected to the liquid product drum;
   s. combining the hydrogen-rich gas and the second liquid stream from the second separator in the rectifier, further purifying the hydrogen-rich gas;
   t. warming the purified hydrogen-rich gas from the rectifier in the heat exchanger to provide a flashed vapor stream;
   u. pumping a third liquid stream from the liquid product drum to the heat exchanger, wherein the third liquid stream is warmed; and
   v. providing a liquid product.

2. The process of claim 1, wherein the heat exchanger comprises one or more brazed aluminum heat exchanger cores.

3. The process of claim 1, wherein the compressed effluent vapor stream comprises hydrogen, paraffinic hydrocarbons, and propylene or isobutylene.

4. The process of claim 1, wherein the compressed effluent vapor stream comprises hydrogen, paraffinic hydrocarbons, and a mixture of propylene and isobutylene.

5. The process of claim 1, wherein the liquid paraffinic stream comprises either propane, isobutane, or a combination of propane and isobutane.

6. The process of claim 1, which includes driving one or more electric generators by the power produced in the first expander, second expander, or both expanders.

7. The process of claim 1, which includes employing a coldbox to contain the heat exchanger, the first separator, the second separator, the liquid product drum, and the rectifier.

8. The process of claim 1, which includes maintaining the liquid product drum at a temperature such that the liquid product drum may be composed of carbon steel.

* * * * *